United States Patent
Murray et al.

(10) Patent No.: US 7,102,038 B2
(45) Date of Patent: Sep. 5, 2006

(54) PHOSPHOROUS REMOVAL AND DIENE REMOVAL, WHEN USING DIENE SENSITIVE CATALYST, DURING CONVERSION OF OLEFINS TO BRANCHED PRIMARY ALCOHOLS

(75) Inventors: Brendan Dermont Murray, Houston, TX (US); Paul Benjerman Himelfarb, Houston, TX (US); Zaida Diaz, Houston, TX (US); David Michael Singleton, Houston, TX (US)

(73) Assignee: Shell Oil Company, Houston, TX (US)

( * ) Notice: Subject to any disclaimer, the term of this patent is extended or adjusted under 35 U.S.C. 154(b) by 907 days.

(21) Appl. No.: 10/216,522

(22) Filed: Aug. 9, 2002

(65) Prior Publication Data

US 2003/0149313 A1 Aug. 7, 2003

Related U.S. Application Data

(63) Continuation-in-part of application No. 09/566,463, filed on May 8, 2000, now Pat. No. 6,492,568, and a continuation-in-part of application No. 09/506,461, filed on May 8, 2000, now Pat. No. 6,566,565, and a continuation-in-part of application No. 09/566,460, filed on May 8, 2000, now Pat. No. 6,653,514.

(51) Int. Cl.
*C07C 27/20* (2006.01)
*C07C 27/22* (2006.01)

(52) U.S. Cl. .................. 568/909; 585/512; 585/328; 585/820; 585/823

(58) Field of Classification Search .............. 568/909; 585/823, 329, 512, 820
See application file for complete search history.

(56) References Cited

U.S. PATENT DOCUMENTS

| | | | |
|---|---|---|---|
| 3,674,886 A | 7/1972 | Komatsu et al. | 260/677 H |
| 3,676,523 A | 7/1972 | Mason | 260/683.15 D |
| 3,686,351 A | 8/1972 | Mason | 260/683.15 D |
| 3,737,475 A | 6/1973 | Mason | 260/683.15 D |
| 3,770,619 A | 11/1973 | Derrien et al. | 208/255 |
| 3,825,615 A | 7/1974 | Lutz | 260/683.15 D |
| 4,020,121 A | 4/1977 | Kister et al. | 260/683.15 D |
| 4,076,842 A | 2/1978 | Plank et al. | 423/328 |
| 4,351,980 A | 9/1982 | Reusser et al. | 585/820 |
| 4,551,443 A | 11/1985 | Hudson | 502/313 |
| 4,717,785 A | 1/1988 | Paxson | 585/823 |
| 5,072,057 A | 12/1991 | Oswald et al. | 568/840 |
| 5,112,519 A | 5/1992 | Giacobbe et al. | 252/174.21 |
| 5,376,393 A | 12/1994 | Nardelli et al. | 426/271 |
| 5,378,439 A | 1/1995 | Delobel et al. | 423/210 |
| 5,510,306 A | 4/1996 | Murray | 502/64 |
| 5,780,694 A | 7/1998 | Singleton | 568/909 |
| 5,849,960 A | 12/1998 | Singleton et al. | 568/909 |
| 5,994,591 A | 11/1999 | Arnoldy et al. | 568/454 |
| 6,084,140 A | 7/2000 | Kitamura et al. | 585/260 |
| 6,388,162 B1 | 5/2002 | Himelfarb et al. | |

FOREIGN PATENT DOCUMENTS

| | | |
|---|---|---|
| EP | 0903333 A1 | 7/1998 |
| EP | 0903333 A1 | 3/1999 |
| WO | WO 01/85651 A2 | 11/2001 |
| WO | WO 01/85654 A2 | 11/2001 |

OTHER PUBLICATIONS

"Verfahren Zur Katalytischen Oligomerisierung Von Monoolefinen" Research Disclosure, Kenneth Mason Publications, Hampshire, GB, No. 415, Nov. 1998 pp. 1445–1451, XP000824939.
"Sasol Detergent Alcohols," Preliminary Sasol R&D Technical Bulletin, Oct. 1995.
International Search Report of Dec. 2, 2003.

*Primary Examiner*—Elvis O. Price

(57) ABSTRACT

A process for making a selectively branched alcohol composition contacting a lower olefin feed comprising linear olefins having at least 3 carbon atoms and a concentration of phosphorous-containing compounds with a sorbent comprising a metal or metal oxide on a support, thereby substantially reducing the concentration of phosphorous-containing compounds and producing a purified lower olefin feed. The purified lower olefin feed is skeletally isomerized and then treated to selectively hydrogenate dienes before hydroformylation to produce selectively branched alcohols.

51 Claims, No Drawings

PHOSPHOROUS REMOVAL AND DIENE REMOVAL, WHEN USING DIENE SENSITIVE CATALYST, DURING CONVERSION OF OLEFINS TO BRANCHED PRIMARY ALCOHOLS

The present application is a continuation-in-part of the following applications: application Ser. No. 09/566,461 (now U.S. Pat. No. 6,653,514); application Ser. No. 09/566,460 (now U.S. Pat. No. 6,566,565); and, application Ser. No. 09/566,463 (now U.S. Pat. No. 6,492,568), all of which were filed May 8, 2000.

FIELD OF THE INVENTION

The invention pertains to a process for removing phosphorous and/or dienes from olefin feeds during their conversion to branched primary alcohols.

BACKGROUND OF THE INVENTION

Depending upon the method of their production, olefin feedstocks may comprise a variety of impurities which have a negative impact upon the catalysts later contacted by the olefin feedstock. Impurities found in olefins that are produced by oligomerization of ethylene units can include phosphorous-containing impurities, including but not necessarily limited to organophosphines and organophosphine oxides. These phosphorous-containing compounds are largely removed from many olefin streams during the process of distillation to separate various "cuts" of olefins. Unfortunately, the organophosphines and organophosphine oxides found in $C_{14}$–$C_{18}$ streams tend to co-distill with the $C_{14}$–$C_{18}$ olefins in the product, making it difficult, if not impossible to remove these phosphine impurities by simple distillation.

$C_6$–$C_{36}$ olefins have utility in the fields of paper and pulp processing, drilling fluids, and machine or metal working oils. Alcohols of such olefins have commercial importance in a variety of applications, including detergents, soaps, surfactants, and freeze point depressants in lubricating oils. These alcohols are produced by a number of commercial processes, such as by oxo or hydroformylation of long chain olefins. In many of these applications, the olefin feedstocks are treated using acid catalysts.

Unfortunately, any basic phosphorus-containing compounds in these olefin feedstocks will negatively affect acid catalysts. The phosphorous-containing moieties that are basic in nature will neutralize the active acid sites of the catalyst, which lowers catalyst activity and performance. The organophosphine moieties may even cause the olefins to oligomerize into undesirable forms.

Dienes are another impurity that negatively impact certain catalysts, in particular, hydroformylation catalysts comprising noble metals, such as palladium. Methods are needed to reduce the phosphorous-content, and the diene content, if desired, of olefin feedstocks.

SUMMARY OF THE INVENTION

The present application provides a process for making a selectively branched alcohol composition, comprising:
 providing a lower olefin feed comprising linear olefins having at least 3 carbon atoms and a concentration of phosphorous-containing compounds;
 contacting said lower olefin feed with a sorbent comprising a metal selected from the group consisting of Sc, Ti, V, Cr, Fe, Co, Ni, Cu, Zn, Zr, Nb, Mn, Ag and combinations thereof on a support in an amount and under sorbing conditions effective to substantially reduce said concentration of said phosphorous-containing compounds in said lower olefin feed, producing a purified lower olefin feed;
 contacting said purified lower olefin feed with a skeletal isomerization catalyst under isomerization conditions effective to produce selectively branched olefins having up to about 36 carbon atoms;
 contacting said selectively branched olefins with a hydrogenation catalyst that is sensitive to diene poisoning in the presence of a gas feed comprising an inert gas and a quantity of hydrogen at a flow rate and under hydrogenation conditions and at a flowrate effective to convert a majority of dienes present in said selectively branched olefins to olefins while producing 1 wt. % or less paraffins, producing purified selectively branched olefins; and
 converting said purified selectively branched olefins to said selectively branched alcohol composition.

DETAILED DESCRIPTION OF EMBODIMENTS

The present application provides a process and sorbents which efficiently and effectively reduce the content of phosphorous-containing compounds and dienes (if present) in olefin streams during the production of selectively branched alcohol compositions.

The process and sorbents described herein may be used to treat substantially any olefin stream. Olefin feedstocks from substantially any source may be treated with sorbents to remove phosphorous and/or dienes. For example, the olefin feed may be derived from: the oligomerization of ethylene; cracking of paraffin wax; the oligomerization of larger olefins than ethylene, preferably olefins having from about 3 to about 6 carbon atoms; the isomerization of alpha olefins; the chlorination-dehydrochlorination of paraffins; paraffin dehydrogenation; Fischer Tropsch synthesis; and, any other methods by which olefins can be synthesized. The olefins in the feed preferably have an average chain length of from about 6 to about 32 carbon atoms, more preferably from about 10 to about 20 carbon atoms, most preferably from about 12 to about 18 carbon atoms.

Specific examples of suitable olefin feeds include, but are not necessarily limited to the Chevron Alpha Olefin product series (trademark of and sold by Chevron Chemical Co.), which are predominantly linear olefins made by the cracking of paraffin wax, which may contain dienes. Also suitable are commercial olefin products manufactured by ethylene oligomerization, marketed in the United States by Shell Chemical Company under the trademark NEODENE and by Ethyl Corporation as Ethyl Alpha-Olefins. Specific procedures for preparing suitable linear olefins from ethylene are described in U.S. Pat. Nos. 3,676,523, 3,686,351, 3,737,475, 3,825,615 and 4,020,121, the teachings of which are incorporated herein by reference. While most of such olefin products are comprised largely of alpha-olefins, other suitable feeds include higher linear internal olefins commercially produced, for example, by the chlorination-dehydrochlorination of paraffins, by paraffin dehydrogenation, and by isomerization of alpha-olefins. These include linear internal olefin products in the C8 to C22 range marketed by Shell Chemical Company and by Liquichemica Company.

An olefin feed generally does not consist of 100% olefins within a specified carbon number range, as such purity is not commercially available. An olefin feed usually is a distribution of mono-olefins having different carbon lengths, with at least 50 wt. % of the olefins being within the stated carbon chain range or digit, however specified. Preferably, the olefin feed contains greater than 70 wt. %, more preferably about 80 wt. % or more of mono-olefins in a specified carbon number range, the remainder of the product being olefin of other carbon number or carbon structure, diolefins, paraffins, aromatics, and other impurities resulting from the synthesis process. The location of the double bond is not limited. The olefin feed composition may comprise α-olefins, internal olefins, or mixtures thereof.

Preferred olefin streams for removal of phosphorous are linear "lower olefin streams" made by oligomerizing ethylene. Some of the known processes for oligomerizing ethylene use organophosphorus compounds that result in phosphorus as a contaminant in the resulting olefin stream. A preferred commercially available olefin feed for the treatment of the present invention is the product marketed in the United States by Shell Chemical Company under the trademark NEODENE®. In a preferred embodiment, the olefin feedstock is treated to remove phosphorous before exposure to an acid catalyst, or before exposure to other conditions which would be adversely affected by the basic nature of phosphorus-containing contaminants. In a preferred embodiment, the content of phosphorous-containing compounds in the "lower olefin feed" is reduced to about 1 ppm or less, preferably about 0.5 ppm or less, most preferably to about 0.1 ppm or less. Given sufficient run time, the sorbents reduce the content of phosphorous-containing compounds in the lower olefin stream to parts per billion (ppb) levels.

In a most preferred embodiment, the olefin stream treated with sorbent(s) to remove phosphorous, herein sometimes called the "lower olefin feed," is the feedstock for the skeletal isomerization catalyst used in the method described in U.S. Pat. No. 5,849,960, which has been incorporated herein by reference. The olefins used in the feed to this skeletal isomerization catalyst are mono-olefins having at least 6 carbon atoms, preferably having from about 11 to about 20 carbon atoms, and most preferably having from about 14 to about 18 carbon atoms. In general, the olefins in the feed to the skeletal isomerization catalyst are predominately linear. While the olefin feed can contain some branched olefins, the olefin feed processed for skeletal isomerization preferably contains greater than about 50 percent, more preferably greater than about 70 percent, and most preferably greater than about 80 mole percent or more of linear olefin molecules.

The catalyst used to treat the feed of linear olefins is effective to skeletally isomerize a linear olefin composition into an olefin composition having an average number of branches per molecular chain of at least 0.7, having less than 0.5 atom % of quaternary carbon atoms, and having at least methyl and ethyl branching. As used herein, the phrase "average number of branches per molecular chain" refers to the average number of branches per alcohol molecule, as measured by $^1H$ and $^{13}C$ Nuclear Magnetic Resonance ($^1H$ and $^{13}C$ NMR), as described in U.S. Pat. No. 5,849,960, incorporated herein by reference. The average number of carbon atoms in the olefin can also be determined by gas chromatography.

Typical olefin feeds also comprise from about 100 to about 2000 ppm dienes. The present application provides methods to reduce the concentration of the dienes in an olefin feed by sorption and/or by selective hydrogenation of the dienes to olefins. For convenience, both process are sometimes collectively referred herein to as "removing" dienes. Preferably, the dienes are removed before the olefin feed is contacted with a catalyst which is adversely affected by dienes, such as a skeletal isomerization catalyst and/or a hydroformylation catalyst. A most preferred embodiment involves selectively hydrogenating dienes in a selectively branched olefin feed before contacting the selectively branched olefin feed with hydroformylation catalysts comprising one or more rare earth metals, particularly palladium, which is sensitive to diene poisoning.

Where the lower olefin feed comprises phosphorus, the sorbent preferably comprises a support which carries a metal, preferably a metal oxide, in order to sorb phosphorus-containing impurities, including but not necessarily limited to organophosphines and organophosphine oxides. The sorbent preferably comprises a support material capable of sorbing dienes, more preferably a neutral or acidic sorbent, most preferably an acidic sorbent. Suitable sorbent support materials include, but are not necessarily limited to alumina, silica, molecular sieves, such as zeolites, activated carbon, aluminosilicate clays, amorphous silicoaluminas, and the like. Suitable support materials for the metal or metal oxide are SELEXSORB AS™, which is commercially available from Alcoa Industrial Chemicals, and KL-5715, which is available from KataLeuna GmBH Catalysts, Germany. A most preferred support material is KL-5715. The sorbent/support preferably removes about 70% or more, preferably about 80% or more, more preferably about 90% or more of the dienes present in the lower olefin feed.

Where the sorbent surface is porous, the pores preferably are sufficiently large to permit entry of diene containing compounds in the feed. Although the surface area of the sorbent is not a critical feature, the surface area preferably is at least about 10 $M^2/g$ in order to provide sufficient contact between the sorbent and the olefin stream. In a preferred embodiment, the sorbent has a surface area of from about 100 $m^2/g$ to about 900 $m^2/g$.

Preferred metals for sorbing phosphorus-containing impurities are transition metals, including but not necessarily limited to those selected from Groups 3–12 of the Periodic Table of the Elements. When the Periodic Table of the Elements is referred to herein, the source of the Periodic Table is: F. Cotton et al. *Advanced Inorganic Chemistry* (5th Ed. 1988), incorporated herein by reference. Groups 3–12 include, but are not necessarily limited to Sc, Y, La, Ac, Hf, Unq, V, Nb, Ta, Unp, Cr, Mo. W, Uhn, Mn, Tc, Re, Uns, Fe, Ru, Os, Co, Rh, Ir, Ni, Pd, Pt, Cu, Ag, Au, Zn, Cd, Hg, Ce, Pr, Nd, Pm, Sm, Eu, Gd, Tb, Dy, Ho, Er, Tm, Yb, Lu, Th, Pa, U, Np, Pu, Am, Cm, Bk, Cf, Es, Fm, Md, No, and Lr. Suitable metals include, but are not necessarily limited to Sc, Ti, V, Cr, Fe, Co, Ni, Cu, Zn, Zr, Nb, Mn, Ag and combinations thereof. Preferred metals are Fe, Co, Ni, Mn, Ag and Cu. In a preferred embodiment, the metal is silver or copper, preferably in the form of oxides. The sorbent suitably comprises from about 0.1 wt. % to about 50 wt. % of the metal oxide of the foregoing metals, preferably copper. Preferably, the sorbent comprises from about 1 wt. % to about 50 wt. %, more preferably from about 5 wt. % to about 35 wt. %, even more preferably from about 8 wt. % to about 20 wt. % of the metal oxide, most preferably from about 8 wt. % to about 10 wt. % of the metal oxide. KL-5715 is a 0.8 mm trilobe shaped aluminum support.

The metal oxide, preferably copper oxide, may be incorporated onto the support using any suitable technique, including but not necessarily limited to ion exchange, co-mulling, or impregnation. A preferred technique is pore volume impregnation using a solution of a copper salt, such as copper nitrate, copper carbonate, or other suitable salts. A preferred salt is copper carbonate. The use of solutions of other Cu salts than copper nitrate may produce a more uniform Cu loading. Copper nitrate is very soluble in water, and tends to wick out of the pores during drying. The result may be more CuO on the outside of the pellets, although smaller pellets are less prone to this effect.

It is preferred for the particles of sorbent to be as small as possible; however, if the size of the particles is too small, the pressure drop through the bed becomes too large. Very small particles also are difficult to retain in the sorbent bed. A preferred particle size is from about 0.05 mm to about 6.5 mm, more preferably from about 0.8 mm to about to about 3 mm. SELEXSORB AS™ is purchased in the form of ⅛ inch spheres, and may be used in the process as purchased. However, spheres are not the most efficient particle shape for purposes of maximizing particle surface to volume ratio. Because of this, if SELEXSORB AS™ is used as the sorbent, it is preferred to grind or otherwise reduce the ⅛ inch spheres into the smallest particles possible without inducing an undue pressure drop or loss of sorbent from the sorbent bed. The particles may have substantially any form, including but not necessarily limited to spherical form, tablet form, cylindrical form, multi-lobed cylindrical forms, and their corresponding hollow counterparts. In a preferred embodiment, the particles have a diameter of from about 50 mesh to about 6 mm, preferably about 0.8 mm (1/32 inch) to about 1.6 mm (1/16 inch), most preferably about 0.8 mm. The length of the particles is not critical, with suitable lengths including, but not necessarily limited to less than about 10 mm, preferably from about 3 mm to about 5 mm.

The sorbent may be contacted with the lower olefin feed in any suitable vessel or arrangement, including a fixed bed, a moving bed, a downflow, an upflow, a concurrent flow, a countercurrent flow, etc. In a preferred embodiment, a column is packed with the sorbent and the olefin feed is passed upflow through the packed bed at a weight hourly space velocity of from about 0.01 to about 100 per hour, preferably at about 0.1 per hour to about 5 per hour, more preferably at about 0.5 per hour. The feed rate is adjusted to sufficiently reduce the level of impurity in the feed to a very low level. The liquid effluent is collected in a container purged with an inert gas, preferably nitrogen, to minimize oxidation.

Where the olefin feed is substantially linear, the olefin feed preferably is subjected to skeletal isomerization. Suitable catalysts for skeletal isomerization contain a zeolite having at least one channel with a crystallographic free channel diameter ranging from greater than 4.2 Å and less than 7 Å., measured at room temperature, with essentially no channel present which has a free channel diameter which is greater than 7 Å. Suitable zeolites are described in detail in U.S. Pat. No. 5,849,960, which has been incorporated herein by reference. Examples of zeolites, including molecular sieves, that can be used in the processes with a channel size between about 0.42 nm and 0.7 nm, include ferrierite, AlPO-31, SAPO-11, SAPO-31, SAPO-41, FU-9, NU-10, NU-23, ZSM-12, ZSM-22, ZSM-23, ZSM-35, ZSM-48, ZSM-50, ZSM-57, SUZ-4, SUZ-4A, SM03, DAF-1, MeAPO-11, MeAPO-31, MeAPO-41, MeAPSO-11, MeAPSO-31, and MeAPSO-41, MeAPSO-46, ELAPO-11, ELAPO-31, ELAPO-41, ELAPSO-11, ELAPSO-31, and ELAPSO-41, laumontite, cancrinite, offretite, hydrogen form of stilbite, the magnesium or calcium form of mordenite and partheite.

Particularly preferred zeolites are those having the ferrierite isotypic framework structure (or homeotypic). See the Atlas of Zeolite Structure Types, by W. M. Meier and D. H. Olson, published by Butterworth-Heinemann, third revised edition, 1992, page 98. The prominent structural features of ferrierite found by x-ray crystallography are parallel channels in the alumino-silicate framework which are roughly elliptical in cross-section. Examples of such zeolites having the ferrierite isotypic framework structure include natural and synthetic ferrierite (can be orthorhombic or monoclinic), Sr-D, FU-9 (EP B-55,529), ISI-6 (U.S. Pat. No. 4,578,259), NU-23 (E.P. A-103,981), ZSM-35 (U.S. Pat. No. 4,016,245) and ZSM-38 (U.S. Pat. No. 4,375,573). A preferred skeletal isomerization catalyst for use in conjunction with the present invention is a hydrogen ferrierite catalyst, as described in U.S. Pat. No. 5,510,306, incorporated herein by reference.

The skeletal isomerization catalyst may be combined with a suitable binder, prepared with an acid, and/or have coke oxidation promoting metals incorporated therein, as described in U.S. Pat. No. 5,849,960. The temperature at which the isomerization may be conducted is from about 200° C. to about 500° C. Temperatures should not exceed the temperature at which the olefin will crack. Suitable pressures maintained during the isomerization reaction are at an olefin partial pressure ranging from 0.1 atmospheres to 10 atmospheres, more preferably from above ½ atmosphere to 5 atmospheres, most preferably above ½ to 2 atmospheres.

The skeletally isomerized olefins, also called "selectively branched olefins," may be converted to any of a broad range of surfactants, including nonionic, anionic, cationic, and amphoteric surfactants, preferably with a degree of branching of at least 0.5, preferably at least about 0.7 and no less than 3. The skeletally isomerized olefin serves as a surfactant intermediate. Specifically, the skeletally isomerized olefins, or selectively branched olefins, serve as the hydrophobic moiety of the surfactant molecule, while the moiety added to the olefin during the conversion process serves as the hydrophile.

Dienes present in the selectively branched olefins preferably are either removed or hydrogenated, and the resulting olefins are then converted to a primary alcohol by hydroformylation. The hydrogenation or removal of dienes also may occur before skeletal isomerization, but preferably occurs after skeletal isomerization. In a preferred embodiment, dienes present in the selectively branched olefins formed during skeletal isomerization are selectively hydrogenated in the presence of a suitable catalyst. In order to accomplish the required selective hydrogenation of dienes to olefins, one of the unsaturated carbon-carbon bonds in the dienes is selectively hydrogenated, leaving a mono-olefin. This selective hydrogenation is accomplished by feeding the lower olefins at a relatively slow (trickle flow) rate to a known, selective hydrogenation catalyst in the presence of a reduced hydrogen content reaction gas.

Any suitable low activity/high selectivity (or "mild") hydrogenation catalyst may be used. Suitable catalysts typically comprise, on a suitable support, a metal selected from Groups 9, 10, or 11 of the Periodic Table of the Elements, F. Cotton et al. *Advanced Inorganic Chemistry* (Fifth Ed. 1998). Preferred metals for use as a catalytic agent in the present process are Co, Ni, Pd, and Pt, most preferably palladium, either alone or alloyed with Ag, Cu, Co, and combinations thereof. The reactivity of the catalyst may be reduced to achieve selectivity by using less of a more active metal on the support or by using a less reactive metal. Where palladium is used as the catalytic agent, the concentration of palladium on a support is from about 0.05 to about 0.5 wt. %, preferably about 0.05 to about 0.2 wt. %.

Examples of suitable supports for the catalytic metal include, but are not necessarily limited to aluminas, silicas, molecular sieves, activated carbon, aluminosilicate clays, and amorphous silicoaluminas, preferably alumna, silica and carbon. Most preferred support materials are alumina and silica. Preferred supports have up to about 15 m²/g surface area, and preferably have from about 2 to about 5 m²/g surface area. A most preferred catalyst for use in the present invention comprises palladium on an alumina support.

It is preferred for the particles of catalyst to be as small as possible; however, if the size of the particles is too small, the pressure drop through the bed becomes too large. The particles may have substantially any form, including but not necessarily limited to spherical form, tablet form, cylindrical form, multi-lobed cylindrical forms, and their corresponding hollow counterparts. In a preferred embodiment, the particles have a diameter of from about 50 mesh (0.05 mm) to about 6.5 mm, preferably about 0.8 mm (1/32 inch) to about 3 mm, most preferably about 0.8 mm. The length of the particles is not critical, with suitable lengths including, but not necessarily limited to less than about 10 mm, preferably from about 3 mm to about 5 mm.

The catalyst may or may not be modified using a suitable promoter, such as chromium, barium, or lanthanium. A preferred promoter is chromium at a preferred concentration of from about 0.05 to about 0.2 wt. %, preferably about 0.05 wt. %. Where chromium is used as a promoter, other suitable additives which may be used at from about 0.05 to 0.25 wt %, preferably about 0.05 wt %, include, but are not necessarily limited to Ba, La, Dy, Ce, Nb, or Sm, preferably Ba or La. A preferred commercially available catalyst is K-8327, a palladium on aluminum catalyst available from W. C. Heraeus GmbH, Catalyst Department PKT, Heraeusstrasse 12-1, D-63450 Hanau, Germany.

The catalysts preferably are used in a fixed bed trickle flow reaction mode. Persons of ordinary skill in the art would expect that a relatively long exposure time between the lower olefins and the catalyst in a trickle flow mode would result in more hydrogenation and an undesirably high production of paraffins in the product. The longer the lower olefins are exposed to the catalyst, the more selective the process is to the production of olefins. This is particularly true at a low gas flow and when the level of hydrogen in the reaction gas is limited, preferably to from about 2 to about 6 vol. %, with the remainder being an inert gas, preferably nitrogen. In other words, the longer the exposure to the catalyst and to a reaction gas having a limited hydrogen content, the higher the conversion of dienes, and the lower the yield of paraffins.

The reaction conditions are relatively mild. The lower olefins preferably are fed to the fixed bed at a liquid hourly space velocity (LHSV) of about 1.0 or less, most preferably about 0.5. The reaction pressure may be ambient, but preferably is maintained relatively low, from about 20 to about 200 psig, most preferably about 30 psig. The reaction temperature also preferably is relatively low, from about 0° C. (32° F.) to about 100° C. (212° F.), preferably from about 26° C. (80° F.) to about 49° C. (120° F.), most preferably about 38° C. (100.4° F.).

Hydroformylation is a term used in the art to denote the reaction of an olefin with CO and $H_2$ to produce an aldehyde/alcohol which has one more carbon atom then the reactant olefin. Frequently, the term hydroformylation is used to cover the aldehyde and the reduction to the alcohol step in total, i.e., hydroformylation refers to the production of alcohols from olefins via carbonylation and an aldehyde reduction process. As used herein, hydroformylation refers to the ultimate production of alcohols. Most commonly used is the "modified Oxo process", using a phosphine, phosphite, arsine or pyridine ligand modified cobalt or rhodium catalyst, as described in U.S. Pat. Nos. 3,231,621; 3,239,566; 3,239,569; 3,239,570; 3,239,571; 3,420,898; 3,440,291; 3,448,158; 3,448,157; 3,496,203; and 3,496,204; 3,501,515; and 3,527,818, the disclosures of which are incorporated herein by reference. Methods of production are also described in Kirk Othmer, "Encyclopedia of Chemical Technology" 3rd Ed. vol. 16, pages 637–653; "Monohydric Alcohols: Manufacture, Applications and Chemistry", E. J. Wickson, Ed. Am. Chem. Soc. 1981, incorporated herein by reference.

Illustrative hydroformylation catalysts include, but are not necessarily limited to, cobalt hydrocarbonyl catalysts and metal-phosphine ligands comprising metals including, but not necessarily limited to palladium, cobalt, and rhodium. The choice of catalysts determines the various reaction conditions imposed, including whether diene removal is advisable. Certain catalysts are not as susceptible to diene poisoning as others. In a preferred embodiment, diene removal is used in conjunction with palladium based catalysts, including, but not necessarily limited to palladium—phosphine ligand catalysts. One of ordinary skill in the art, by referring to any of the well-known literature on oxo alcohols, can readily determine the conditions of temperature and pressure that will be needed to hydroformylate the olefins. An example in addition to U.S. Pat. No. 5,849,960 is EP 0 903 333 A1, incorporated herein by reference.

Temperatures can range from about room temperature to about 300° C. Typical reaction conditions are moderate, with temperatures of from about 125° C. to about 200° C. Reaction pressures range from about 300 psig to about 1500 psig, although lower or higher pressures may be selected. The catalyst to olefin ratio is from about 1:1000 to about 1:1. The ratio of hydrogen to carbon monoxide can vary widely, but usually is from about 1 to about 10, preferably from about 2 moles of hydrogen to one mole of carbon monoxide to favor the alcohol product.

The hydroformylation can be carried out in the presence of an inert solvent, although solvent is not necessary. A variety of solvents can be used, including but not necessarily limited to: ketones, e.g. acetone, methyl ethyl ketone, methyl isobutyl ketone, acetophenone and cyclohexanone; aromatic compounds such as benzene, toluene and the xylenes; halogenated aromatic compounds such as chlorobenzene and orthodichlorobenzene; halogenated paraffinic hydrocarbons such as methylene chloride and carbon tetrachloride; paraffins such as hexane, heptane, methylcyclohexane and isooctane; and, nitriles, such as benzonitrile and acetonitrile.

Suitable catalyst ligands include, but are not necessarily limited to tertiary organo phosphines, such as trialkyl phosphines, triamyl phosphine, trihexyl phosphine, dimethyl ethyl phosphine, diamylethyl phosphine, tricyclopentyl(or hexyl) phosphine, diphenyl butyl phosphine, diphenyl benzyl phosphine, triethoxy phosphine, butyl diethyoxy phosphine, triphenyl phosphine, dimethyl phenyl phosphine, methyl diphenyl phosphine, dimethyl propyl phosphine, the tritolyl phosphines and the corresponding arsines and stibines. Included as bidentate-type ligands are tetramethyl diphosphinoethane, tetramethyl diphosphinopropane, tetraethyl diphosphinoethane, tetrabutyl diphosphinoethane, dimethyl diethyl diphosphinoethane, tetraphenyl diphosphinoethane, tetraperfluorophenyl diphosphinoethane, tetraphenyl diphosphinopropane, tetraphenyl diphosphinobutane, dimethyl diphenyl diphosphinoethane, diethyl diphenyl diphosphinopropane and tetratrolyl diphosphinoethane.

Examples of other suitable ligands include, but are not necessarily limited to the phosphabicyclohydrocarbons, such as 9-hydrocarbyl-9-phosphabicyclononane in which the smallest P-containing ring contains at least 5 carbon atoms.

The branched primary alcohol compositions produced from the olefin feeds treated herein are suitable for the manufacture of anionic, nonionic, and cationic surfactants, preferably the former two, more preferably the anionic. Specifically, the branched primary alcohol compositions are useful as the precursor for the manufacture of anionic sulfates, including alcohol sulfates and oxyalkylated alcohol sulfates, and nonionic oxyalkylated alcohols.

The invention will be better understood with reference to the following examples, which are illustrative only and should not be construed as limiting the invention to a particular embodiment.

EXAMPLE I

A variety of materials were studied as sorbent beds for removing phosphorus impurities. A C16 olefin feed having a density of 0.78 g./cc. and comprising 20.2 ppm phosphorus was fed to a reactor tube having a diameter of 1.73 cm. at a target flow rate of 54 g./hr. The reactor tube was partially filled, to about 50 cm$^3$, with the test sorbent. In this experiment, the test sorbent was ALCOA 946 (CuO/Al$_2$O$_3$) (⅛" spheres). Samples were taken at various times and the parameters given in the following Table were recorded:

| Elapsed time (hr.) | Product Collected (g.) | Fluid flow (g./hr.) | ppm P in fluid coming out of bed |
|---|---|---|---|
| 0 | 0 | | 1.6 |
| 2 | 136.4 | 68.20 | 1.8 |
| 18.5 | 812.5 | 40.98 | 3.4 |
| 25.5 | 1184.7 | 53.17 | 3.9 |
| 42.5 | 2204.5 | 59.99 | 7.3 |
| 49.5 | 2602.7 | 56.89 | 11.1 |
| 66.5 | 3397.1 | 46.73 | 11.6 |
| 73.5 | 3718.4 | 45.90 | 12.1 |
| 90.5 | 3831.8 | 6.67 | 12.5 |
| 96.5 | 4109.8 | 46.33 | 16.1 |
| 116 | 5194.8 | 55.64 | 17.1 |
| 125 | 5534.8 | 37.78 | 17 |

The sorbent removed 50% of the phosphorus from the feedstock for about 60 bed volumes. At the flow conditions of the test, the relatively large spheres of sorbent were not able to lower phosphorus to <0.5 ppm.

EXAMPLE II

A C16 olefin feed having a density of 0.78 g./cc. and comprising 20.2 ppm of phosphorus was fed to a reactor tube having a diameter of 1.73 cm at a target flow rate of 54 g./hr. The reactor tube was partially filled with the test sorbent. In this experiment, the test sorbent was "AX-200," a trilobe alumina having a particle size of about ½2" supplied by Criterion Catalyst Company. Samples were taken at various times and the following results recorded:

| Elapsed time (hr) | Gm Product Collected | Fluid Flow (gm/hr) | ppm P in fluid coming out of bed |
|---|---|---|---|
| 0 | 0 | | 0.1 |
| 2 | 117.2 | 58.6 | 0.5 |
| 18.5 | 1089.6 | 58.93 | 1.7 |
| 25.5 | 1506.2 | 59.51 | 7.8 |
| 42.5 | 2482. | 57.42 | 17.6 |
| 49.5 | 2833.4 | 50.16 | 22.2 |
| 66.5 | 3730.6 | 52.78 | 29.5 |
| 73.5 | 4018.9 | 41.19 | 28.8 |
| 90.5 | 4115.3 | 5.67 | 23.8 |
| 96.5 | 4421.3 | 51.00 | 23.4 |
| 116 | 5675.3 | 64.31 | 21.9 |
| 125 | 6115.3 | 48.89 | 20.6 |

The small, multilobed particles of sorbent successfully removed substantially all of the phosphorus from the feedstock for about 3 bed volumes, and removed 50% of the phosphorus in the feed for about 40 bed volumes.

EXAMPLE III

A C16 olefin feed having a density of 0.78 g./cc and comprising 22.6 ppm phosphorus was fed to a reactor tube having a diameter of 1.73 cm at a target flow rate of 30 g./hr. The reactor tube was partially filled, to about 50 cm$^3$, with the test sorbent. The test sorbent was crushed and sieved CuO on AX-200 having a particle size of about 14–24 mesh. Samples were taken at various times and the following results recorded:

| Elapsed time (hr.) | Product Collected (g.) | Fluid Flow (g./hr.) | ppm P in fluid coming out of bed |
|---|---|---|---|
| 0 | | | |
| 17.25 | 719.7 | 41.72 | 0.1 |
| 65.25 | 2098.7 | 28.73 | <0.1 |
| 137.75 | 3967.7 | 25.78 | <0.1 |
| 185.75 | 5069.7 | 22.96 | 1.3 |
| 210.25 | 5639.7 | 23.27 | 3.3 |
| 234.25 | 6189.7 | 22.92 | 6.6 |
| 267 | 7003.7 | 24.85 | 10.6 |
| 305.25 | 7993.7 | 25.88 | 11.9 |
| 330.25 | 8630.7 | 25.48 | 14.6 |

The small, multilobed particles of sorbent successfully removed substantially all of the phosphorus from the feedstock for about 125 bed volumes.

EXAMPLE IV

Example III was repeated using 9% CuO on AX-300 (1/20" trilobe extrudate obtained from Criterion Catalyst Company). Samples were taken at various times and the following results were recorded:

| Elapsed time (hr) | Gm Product Collected | Fluid Flow (gm/hr) | ppm P in fluid coming out of bed |
|---|---|---|---|
| 0 | | | |
| 17.25 | 625.3 | 36.25 | 0.1 |

-continued

| Elapsed time (hr) | Gm Product Collected | Fluid Flow (gm/hr) | ppm P in fluid coming out of bed |
|---|---|---|---|
| 65.25 | 2064.3 | 29.98 | 0 |
| 137.75 | 3752.3 | 23.28 | 0.4 |
| 185.75 | 4810.3 | 22.04 | <0.1 |
| 210.25 | 5375.3 | 23.06 | 3.2 |
| 234.25 | 5951.3 | 24.00 | 6.8 |
| 267 | 6839.3 | 27.11 | 11.6 |
| 305.25 | 7915.3 | 28.13 | 16.9 |
| 330.25 | 8581.3 | 26.64 | 18.9 |

The intermediate sized, multilobed particles of sorbent successfully removed substantially all of the phosphorus from the feedstock for about 130 bed volumes.

EXAMPLE V

Example III was repeated using 18% CuO/AX-300 (1/20" trilobe extrudate). Samples were taken at various times and the following results were recorded:

| Elapsed time (hr.) | Product Collected (g.) | Fluid Flow (g./hr) | ppm P in fluid coming out of bed |
|---|---|---|---|
| 0 | | | |
| 17.25 | 798.7 | 46.30 | 0.1 |
| 65.25 | 2540.7 | 36.29 | 0.1 |
| 137.75 | 4275.7 | 23.93 | 0.4 |
| 185.75 | 5500.7 | 25.52 | 3.1 |
| 210.25 | 6100.7 | 24.49 | 5.5 |
| 234.25 | 6682.7 | 24.25 | 8.3 |
| 267 | 7600.7 | 28.03 | 13.1 |
| 305.25 | 8680.7 | 28.24 | 17.7 |
| 330.25 | 9410.7 | 29.20 | 19.9 |

The sorbent, which had a size and shape similar to that in Example IV, successfully removed substantially all of the phosphorus from the feedstock for about 130 bed volumes. No additional capacity was observed with the higher metal loading (9 wt. % in Example IV vs. 18 wt. % in Example V).

EXAMPLE VI

A C16 olefin feed having a density of 0.78 gm/cc and comprising 10.5 ppm phosphorus was fed to a reactor tube having a diameter of 1.73 cm at a target flow rate of 30 gm/hr. The reactor tube was partially filled with the test sorbent 50 cm³. The test sorbent was 9% CuO/AX200, which has a particle size of about 1/32" trilobe extrudate. Samples were taken at various times and the following results were recorded:

| Elapsed time (hr) | Gm Product Collected | Fluid Flow (gm/hr) | ppm P in fluid coming out of bed |
|---|---|---|---|
| 0 | | | |
| 18.5 | 558.8 | 30.21 | 1 |
| 43 | 1163.8 | 24.69 | <0.1 |
| 139.5 | 2960.8 | 18.62 | 0.1 |
| 163 | 3706.8 | 31.74 | <0.1 |
| 186.75 | 4435.8 | 30.69 | 0.1 |
| 210.75 | 5119.8 | 28.50 | <0.1 |
| 241.25 | 5953.8 | 27.34 | 0.1 |
| 307.5 | 7747.8 | 27.08 | <0.1 |

-continued

| Elapsed time (hr) | Gm Product Collected | Fluid Flow (gm/hr) | ppm P in fluid coming out of bed |
|---|---|---|---|
| 331 | 8469.8 | 30.72 | <0.1 |
| 379.5 | 9924.6 | 30.00 | 0.1 |
| 427 | 11073.6 | 24.19 | 0.3 |
| 474.75 | 12184.6 | 23.27 | 0.6 |
| 523.2 | 13440.6 | 25.90 | 1.3 |

The small, multilobed sorbent successfully removed substantially all of the phosphorus from the feedstock for about 275 bed volumes.

EXAMPLE VII

The procedures of Example VI were repeated using 9% CuO on AX-300 (1/20"). The results are given in the following Table:

| Elapsed time (hr) | Gm Product Collected | Fluid Flow (gm/hr) | ppm P in fluid coming out of bed |
|---|---|---|---|
| 0 | | | 0.1 |
| 18.5 | 545.3 | 29.48 | 0 |
| 43 | 1220.3 | 27.55 | 0 |
| 139.5 | 2415.3 | 12.38 | 0.1 |
| 163 | 3036.3 | 26.43 | 0 |
| 186.75 | 3676.3 | 26.95 | 0.1 |
| 210.75 | 4340.3 | 27.67 | 0.1 |
| 241.25 | 5185.3 | 27.70 | 0.2 |
| 307.5 | 6989.3 | 27.23 | 1 |
| 331 | 7743.3 | 32.09 | 1.1 |
| 379.5 | 9127.6 | 28.54 | 1.8 |
| 427 | 10400.6 | 26.80 | 2.6 |
| 474.75 | 11660.6 | 26.39 | 2.8 |
| 523.25 | 12947.6 | 26.54 | |

The intermediate sized, multilobed particles of sorbent successfully removed substantially all of the phosphorus from the feedstock for about 170 bed volumes. The larger size particles produced a lower capacity at the same target flow rate as Example VI using the same phosphorus containing feedstock.

EXAMPLE VIII

A series of experiments was performed to demonstrate higher temperature performance (80° C. and 120° C.) using 1/32" trilobe sorbent particles. A C16 olefin feed having a density of 0.78 gm/cc and comprising 20 ppm phosphorus was fed to a reactor tube having a diameter of 1.73 cm at a target flow rate of 23 gm/hr. The reactor tube was partially filled with the test sorbent. The test sorbent was 9% CuO/AX300, which has a particle diameter of about 1/32" as a trilobe extrudate. The temperature in the reactor tube was maintained at 80° C. Samples were taken at various times and the following results were recorded:

| Elapsed time (hr) | Gm Product Collected | Fluid Flow (gm/hr) | ppm P in fluid coming out of bed |
|---|---|---|---|
| 0 | | | |
| 3.25 | 76.2 | 23.45 | 0.2 |
| 5.75 | 119.6 | 17.36 | 0.2 |

-continued

| Elapsed time (hr) | Gm Product Collected | Fluid Flow (gm/hr) | ppm P in fluid coming out of bed |
|---|---|---|---|
| 22.5 | 438.3 | 19.03 | 0 |
| 29.5 | 552.1 | 16.26 | 0.1 |
| 45.5 | 665.5 | 7.09 | — |
| 53.5 | 869.5 | 25.50 | 0.1 |
| 71.5 | 1393.8 | 29.13 | 0.1 |
| 80.25 | 1638.3 | 27.94 | 0 |
| 95.75 | 1747.7 | 7.06 | — |
| 103.75 | 1954.3 | 25.83 | 0 |
| 119.75 | 2555.8 | 37.59 | 0 |
| 141.75 | 3322.7 | 34.86 | 0.1 |
| 149.75 | 3565.7 | 30.37 | 0 |
| 165.75 | 4064.2 | 31.16 | 0 |
| 174.5 | 4302.9 | 27.28 | 0 |
| 189.75 | 4747.7 | 29.17 | 0 |
| 197.75 | 4969.4 | 27.71 | 0.1 |
| 213.75 | 5432.6 | 28.95 | 0.2 |
| 237.75 | 6126.3 | 28.90 | 0.7 |
| 244.75 | 6322.5 | 28.03 | 1.2 |
| 264.25 | 6887.7 | 28.98 | 3 |
| 271.5 | 7031.1 | 19.78 | |
| 288.5 | 7032.1 | 0.06 | 10.8 |
| 295.5 | 7342.8 | 44.39 | 5.2 |
| 309.75 | 7837.5 | 34.72 | 7.3 |
| 316.5 | 8059.4 | 32.87 | 10.2 |
| 334 | 8667.1 | 34.73 | |
| 341 | 8908.2 | 34.44 | |

Even at the higher temperature, the sorbent successfully removed substantially all of the phosphorus from the feedstock for about 150 bed volumes.

EXAMPLE IX

The procedures of Example VIII were repeated at a temperature of 120° C. The results appear in the following Table:

| Elapsed time (hr) | Gm Product Collected | Fluid Flow (gm/hr) | ppm P in fluid coming out of bed |
|---|---|---|---|
| 0 | | | |
| 3.25 | 103.2 | 0.00 | 0.1 |
| 5.75 | 160 | 22.72 | 0.1 |
| 22.5 | 566.7 | 24.28 | 0.1 |
| 29.5 | 686.5 | 17.11 | 0.1 |
| 45.5 | 788.6 | 6.38 | — |
| 53.5 | 827.1 | 4.81 | 0.1 |
| 71.5 | 1364.7 | 29.87 | 0.4 |
| 80.25 | 1614.7 | 28.57 | 0.4 |
| 95.75 | 1986.5 | 23.99 | 0.3 |
| 103.75 | 2178.4 | 23.99 | 0.3 |
| 119.75 | 2570.1 | 24.48 | 0.3 |
| 141.75 | 3107.9 | 24.45 | 0.3 |
| 149.75 | 3298.4 | 23.81 | 0.2 |
| 165.75 | 3689.4 | 24.44 | 0.3 |
| 174.5 | 3892.1 | 23.17 | 0.2 |
| 189.75 | 4270.7 | 24.83 | 0.3 |
| 197.75 | 4459.8 | 23.64 | 0.2 |
| 213.75 | 4854.5 | 24.67 | 0.3 |
| 237.75 | 5443.7 | 24.55 | 0.6 |
| 244.75 | 5611.2 | 23.93 | 0.9 |
| 264.25 | 6091.1 | 24.61 | 3.8 |
| 271.5 | 6260 | 23.30 | |
| 288.5 | 6683.8 | 24.93 | 10.8 |
| 295.5 | 6848.6 | 23.54 | 13.1 |
| 309.75 | 7193 | 24.17 | 7.3 |
| 316.5 | 7348.4 | 23.02 | 22.2 |
| 334 | 7772.8 | 24.25 | |
| 341 | 7941.6 | 24.11 | |

Again, the higher temperature did not interfere with successful removal of substantially all of the phosphorus from the feedstock for about 140 bed volumes.

EXAMPLE X

NEODENE 16 containing 18 ppm phosphorus was placed in a jar with sorbent and shaken intermittently by a flat bed shaker over a period of 15 hours at 23° C. to achieve equilibration. The NEODENE to sorbent weight ratios used was 100. After equilibration, the NEODENE was separated from the sorbent and analyzed for phosphorus using inductively coupled plasma analytical method (ICP). The results are given in the following Table:

| Sorbent | Equilibrium P (ppm) | P loading (g/100 g sorbent) |
|---|---|---|
| BARNABEY SE carbon | 7 | 0.11 |
| BARNABEY CE carbon | 3 | 0.15 |

EXAMPLE XI

The following examples illustrate the nature of the invention and its impact on skeletal isomerization of detergent range olefins.

A glass column with an inner diameter of 50 mm was packed with 3.2 mm Selexsorb AS spheres obtained from Alcoa Company of America to produce a bed 400 mm in length. 20 liters of NEODENE® 16 olefin, a $C_{16}$ linear, alpha olefin commercially available from Shell Chemical Company, was passed through the packed bed of Selexsorb AS spheres at a weight hourly space velocity of 0.01 per hour and the liquid effluent was collected in a container purged with nitrogen. The phosphorus content of the NEODENE® 16 olefin was reduced from 20 ppm to 0.2 ppm in the process.

EXAMPLE XII

A catalyst was prepared in accordance with Example C of U.S. Pat. No. 5,510,306, which has been incorporated herein by reference and is reproduced in part herein for convenience. An ammonium-ferrierite having a molar silica to alumina ratio of 62:1, a surface area of 369 square meters per gram (P/Po=0.03), a soda content of 480 ppm and n-hexane sorption capacity of 7.3 g per 100 g of zeolite was used as the starting zeolite. The catalyst components were mulled using a Lancaster mix muller. The mulled catalyst material was extruded using a 2.25 inch Bonnot pin barrel extruder.

The catalyst was prepared using 1 weight percent acetic acid and 1 weight percent citric acid. The Lancaster mix muller was loaded with 645 grams of ammonium-ferrierite (5.4% LOI) and 91 grams of CATAPAL D® alumina (LOI of 25.7%). The alumina was blended with the ferrierite for 5 minutes during which time 152 milliliters of de-ionized water was added. A mixture of 6.8 grams glacial acetic acid, 7.0 grams of citric acid and 152 milliliters' of de-ionized water was added slowly to the muller in order to peptize the alumina. The mixture was mulled for 10 minutes. 0.20 Grams of tetraammine palladium nitrate in 153 grams of de-ionized water were then added slowly as the mixture was mulled for a period of 5 additional minutes. Ten grams of METHOCEL F4M® hydroxypropyl methylcellulose was added and the zeolite/alumina mixture was mulled for 15 additional minutes. The extrusion mix had an LOI of 43.5%.

The 90:10 zeolite/alumina mixture was transferred to the 2.25 inch Bonnot extruder and extruded using a die plate with 1/16" holes.

The moist extrudates were tray dried in an oven heated to 150° C. for 2 hours, and then increased to 175° C. for 4 hours. After drying, the extrudates were broken manually. The extrudates were calcined in flowing air at 500° C. for two hours.

EXAMPLE XIII

Skeletal Isomerization of the NEODENE® 16 olefin was conducted using an olefin isomerization reactor. A stainless steel tube, 25.4 mm OD, 15 mm ID and 685 mm long was used to contain the catalyst. One end of the tube was screwed into a stainless steel head equipped with a thermowell which extended up the center of the tube. The tube was loaded with a small plug of glass wool, then filled to a depth of 150 mm with 20 mesh silicon carbide, and then a small plug of glass wool was added above the SiC. 6.00 grams of the catalyst described in Example XII was admixed with 45 grams of 60–80 mesh SiC and added in three parts to distribute it evenly inside the reactor tube. Another piece of glass wool was added and the remaining volume of the reactor tube was filled with 20 mesh SiC topped by a final piece of glass wool. The tube was screwed into another stainless steel head and a multipoint thermocouple was inserted into the thermowell to allow the temperature above, below and inside the catalyst bed to be monitored. The reactor tube was then installed inside an electric furnace. Connections were made at the top of the reactor to allow nitrogen and the olefin to be passed through the reactor. The bottom of the reactor was connected to a condenser and a product collection system.

Nitrogen at a rate of 6 liters per hour was passed through the reactor while the catalyst bed was heated to 290° C. over a period of 2 hours. NEODENE® 16 olefin with a phosphorus content of 20 ppm and 0.2 ppm was pumped to the reactor at a rate of 60.0 grams per hour, allowed to mix with the incoming nitrogen and then passed through the catalyst bed. During the testing the inlet pressure was held at 1.6 psig while the outlet pressure of the reactor was maintained at 1.0 psig. The liquid product was collected in a 5 gallon vessel while the uncondensed gas was passed through a gas meter. Sampling ports incorporated in the reactor allowed the liquid and gas products to be analyzed regularly. The products were analyzed by gas chromatography. The results of the testing are presented in the following Table.

TABLE

The Effect of the Phosphorus Content in NEODENE® 16 linear alpha olefin on the Degree of Branching During Skeletal Olefin Isomerization

| | Olefin Used Phosphorus Content | |
| --- | --- | --- |
| Time On Stream, Hr | Treated NEODENE® 16 0.2 ppm % Branching In Liquid Product | Untreated NEODENE® 16 20 ppm |
| 13.5 | 97 | 81 |
| 24.5 | 97 | 68 |
| 37.8 | 97 | 56 |
| 64.0 | 97 | 33 |
| 110 | 97 | 20 |
| 230 | 96 | Stopped Test after 110 hours |

In the presence of 20 ppm of phosphorous in the untreated NEODENE®16, the degree of branching declined rapidly with time on stream. In the case of the treated stream, where the phosphorus was reduced to 0.2 ppm, the degree of branching stayed much higher for a much longer time on stream.

EXAMPLE XIV

The procedures of Example X were repeated using a feed containing 20 ppm P, a NEODENE® 16 to sorbent weight ratio of 100 using the following sorbents. The results are shown in the following Table:

| Sorbent | Equilibrium P (ppm) | P loading (g/100 g sorbent) |
| --- | --- | --- |
| SELEXSORB AS ™ | 0.5 | 0.16 |
| Ag mordenite (15–20% Ag) | 16 | 0.04 |
| Ag X-zeolite (35% Ag) | <2 | >0.18 |

The procedures of Example X were repeated except the feed contained 16 ppm P. The results are shown in the following Table:

| Sorbent | NEODENE® to sorbent weight ratio | Equilibrium P (ppm) | P loading (g/100 g sorbent) |
| --- | --- | --- | --- |
| Ag mordenite (15–20% Ag) | 100 | 11.2 | 0.05 |
| Ag X-zeolite (35% Ag) | 400 | 6.3 | 0.39 |

In the above Tables, the X-zeolite, which contains larger pores than the mordenite, allows for uptake of a greater amount of the bulky phosphorus containing compounds. Also, the load of Ag on the zeolite was higher, which increased the phosphorus uptake. The Ag X-zeolite and the AS SELEXSORB™ both performed very well.

EXAMPLE XV

A series of tests were performed to illustrate the impact of diene removal on skeletal isomerization of detergent range olefins.

A. Preparation of Treated Feed

A glass column with an inner diameter of 50 mm was packed with 150 mesh neutral, activated aluminum oxide (Brockmann I) obtained from Aldrich Chemical Company to produce a bed 400 mm in length. 20 liters of a mixture of primarily linear $C_{14-19}$ olefins, obtained from and commercially available from Shell Chemical Company, was passed through the packed bed at a weight hourly space velocity of 0.5 per hour and the liquid effluent was collected in a container purged with nitrogen. The diene content of the mixed $C_{14}$–$C_{19}$ olefins was reduced from 270 ppm to 20 ppm in the process.

B. Preparation of Skeletal Isomerization Catalyst

A catalyst was prepared using the procedures described in Example 12.

C. Skeletal Isomerization Using Treated Feed from A

Skeletal isomerization of the mixture of alumina treated $C_{14}$–$C_{19}$ olefins obtained in part A of this Example was performed as outlined in Example XIII.

The mixture of $C_{14}$–$C_{19}$ olefins, prepared as in Section A (with diene content of 20 ppm), was pumped to the reactor at a rate of 60.0 grams per hour, allowed to mix with the incoming nitrogen and then passed through the catalyst bed. During the testing the inlet pressure was held at 1.6 psig while the outlet pressure of the reactor was maintained at 1.0 psig. The liquid product was collected in a 5 gallon vessel while the uncondensed gas was passed through a gas meter. Sampling ports incorporated in the reactor allowed the liquid and gas products to be analyzed regularly. The products were analyzed by gas chromatography. The results of the testing are presented in the Table below.

| Feedstock | Untreated Mixture of Linear $C_{14}$–$C_{19}$ Olefins | Alumina Treated $C_{14}$–$C_{19}$ Olefins | Selectively Hydrogenated $C_{14}$–$C_{19}$ Olefins |
|---|---|---|---|
| Diene Content | 270 | 20 | 160 |
| Time on Stream Hr. | % Branching In Liquid Product | | |
| 18 | 82 | 94 | 93 |
| 42 | 77 | 93 | 92 |
| 70 | 64 | 92 | 90 |
| 91 | 54 | 91 | 88 |
| 114 | 48 | 90 | 85 |
| 135 | 43 | 88 | 82 |

The level of branching in the isomerized product was significantly higher when the dienes were first sorbed by passage of the $C_{14}$–$C_{19}$ olefins through an alumina bed.

EXAMPLE XVI

A glass column with an inner diameter of 50 mm was packed with 150 mesh neutral, activated aluminum oxide (Brockmann I) obtained from Aldrich Chemical Company to produce a bed 400 mm in length. 20 L of a mixture of primarily linear $C_{14-19}$ olefins, obtained from and commercially available from Shell Chemical Company, was passed through the packed bed at a weight hourly space velocity of 0.5 per hour and the liquid effluent was collected in a container purged with nitrogen. The diene content of the mixed $C_{14}$–$C_{19}$ olefins was reduced from 270 ppm to 20 ppm in the process.

EXAMPLE XVII

A glass column with an inner diameter of 50 mm was packed with 150 mesh neutral, activated aluminum oxide (Brockmann I) obtained from Aldrich Chemical Company to produce a bed 400 mm in length. Olefins were prepared using the method of Example V and distilled to obtain a mixture of $C_{14}$–$C_{18}$ selectively branched olefins. The selectively branched olefins were passed through the packed bed at a weight hourly space velocity of 0.1 per hour and the liquid effluent was collected in a container purged with nitrogen. The diene content of the selectively branched olefins was reduced from 240 ppm to 24 ppm in the process.

EXAMPLE XVIII

A conventional type catalyst used for removing (hydrogenating) dienes in pyrolysis gasoline(~carbon $C_5$–$C_{10}$) was used to determine hydrogenation specificity. The catalyst employed contained (0.5 wt % Pd on alumina). The catalyst was used in a trickle-flow reactor at 38° C. (100° F.), 5 kPa (30 psig), with 25 cc catalyst using a $C_{13}/C_{14}$ liner olefin feed with approximately 500 ppm dienes

| Hydrogen (1/hr) | Dienes Removed (% conversion) | Paraffin Make Wt % |
|---|---|---|
| 3.80 | 55 | 13.6 |
| 0.20 | 34 | 7.9 |
| 0.14 | 28 | 6.6 |
| 0.02 | 18 | 0.3 |

Although it appears that target diene removal (or hydrogenation) can be reached, the removal (or hydrogenation) does not appear to be sufficiently selective. At low hydrogen flows, to minimize paraffin make, diene removal was not sufficient. It was decided that a more selective catalyst is required.

EXAMPLE XIX

A batch reactor was used to screen a number of different catalysts: 500 ml reactor; 350 ml $C_{13}/C_{14}$ linear olefin feed; 38.33 kPa (230 psig) with 6% $H_2$ in $N_2$; 1000 rpm; ~24° C. (75° F.). Representative results (paraffin make) are given below for 40% diene removal.

| Catalyst | Volume Cat Cc | Surface Area m2/g | Particle Shape and Size | Pd Loading wt % | Paraffin Make wt % |
|---|---|---|---|---|---|
| HEREAUS CHP-13 ™ | 9 | 110 | 2.5 mm sphere | 0.4 | 1.2 |
| CALSICAT E144 ™ | 9 | 40 | 2.5 mm sphere | 0.5 | 0.9 |
| HEREAUS K8327 ™ | 9 | 5 | 2.5 mm sphere | 0.2 | 0.5 |
| In-house 1 | 9 | 14 | 2.5 mm trilobe | 0.05 | 0.7 |
| In-house 2 | 30 | 10 | 2.5 mm trilobe | 0.05 | 0.5 |
| In-house 3 | 30 | 6 | 2.5 mm trilobe | 0.05 | 0.3 |

Increased selectivity (lower paraffin make) was obtained with low surface area <15 m2/2 g and lower Pd loading <0.5 wt %.

The in-house developed catalysts were prepared as follows: commercially available alumina powder was obtained from Criterion Catalysts and Technology. The powder was calcined at high temperature from 1100° C. to 1300° C. to obtain the desired surface of between 14 m2/g and 6 m2/g. The calcined powder was extruded in a typical manner into 2.5 mm trilobe extrudates. These extrudates were impregnated with palladium (0.05 wt %) and were further promoted with chromium (0.05 wt %), as described in U.S. Pat. No. 4,551,443, incorporated herein by reference, using 0.05 wt. % Ba as an additive.

Of the commercial catalysts tested, HEREAUS K8327 gave the best results. The catalyst was used in subsequent process optimization in continuous operation and commercialization studies, although any of the catalysts would be suitable.

EXAMPLE XX

Once Hereaus K8327 was identified as a suitable commercially available catalyst, process conditions were varied to optimally balance activity and selectivity. The effect of hydrogen flow (GHSV-gas hourly space velocity) for $C_{13}/C_{14}$ and $C_{11}/C_{12}$ linear feeds is given below, where the hydrogen was diluted with nitrogen in (6% $H_2/N_2$). (GHSV is defined as the vol. feed/vol. cat. hr.). The range of hydrogen dilution ranged from 2% to 6% and 6% was found preferred. For the $C_{11}/C_{12}$ example, the results are given for two different feed flows of WHSV equal 2 and 1. (The WHSV is defined by g. feed/g. cat. hr).

| GHSV hr-1 | Diene Conv. % | Paraffin Make Wt % |
|---|---|---|
| C13/C14 Feed, WHSV = 2: | | |
| 15 | 26 | 0.6 |
| 30 | 32 | 0.7 |
| 35 | 35 | 0.8 |
| 45 | 32 | 1.1 |
| 75 | 35 | 1.4 |
| C11/C12 Feed, WHSV = 2: | | |
| 12 | 31 | 0.36 |
| 25 | 39 | 0.59 |
| 45 | 47 | 0.83 |
| C11/C12 Feed, WHSV = 1: | | |
| 8 | 55 | 0.4 |
| 25 | 53 | 1.1 |

Results from the $C_{13}/C_{14}$ feed show that there is an optimal gas flow, above which excess paraffins are made with no significant increase in diene removal (hydrogenation). The optimal gas flow also depends on the type of feed used, as shown later. Under the condition above at GHSV equal to 35 for the $C_{13}/C_{14}$ feed, a longer-term test was performed to check catalyst stability. The test run was carried out for approximately 2000 hr with no significant catalyst performance change.

Results show that dienes are more easily and selectively hydrogenated in the $C_{11}/C_{12}$ feeds than from the $C_{13}/C_{14}$ feed. One factor affecting activity is the concentration of alpha olefins (AO's), as compared to internal olefins. High AO feeds (~20–50%) typically had about 10–20% less hydrogenation respectively and the $C_{11}/C_{12}$ feed had the lowest AO content (~6%).

The use of lower feed flows combined with lower gas flows resulted in an activity improvement and a dramatic selectivity improvement.

EXAMPLE XXI

Initial results on branched feeds are shown below, as determined in a batch reactor. (The conditions of the batch reactor were the same as those given for linear feeds with the Heraeus K8327 catalyst). The feed contained approximately 520 ppm dienes. The results are broken-out depending on the carbon number, as shown below.

|  | Total Dienes | C15–C16 Component | C8–C14 Component |
|---|---|---|---|
| Diene Removal % | 61% | 49% | 90% |

From the foregoing results, it appears that dienes can be effectively hydrogenated in branched feeds as well as linear feeds. The dienes in lighter feeds were hydrogenated more easily than the dienes in heavier feeds. (Note that by topping the feed, or separating the different olefins based on their carbon number, the lighter components were removed to the degree desired, as is done in the commercial process).

EXAMPLE XXII

Hydrogenation of dienes was performed in a continuous trickle flow reactor at the GHSV (G) and WHSV (W) shown below, along with the results:.

| Reactor Conditions | Total Dienes Removed % | C15–C16 Dienes Removed % | C8–C14 Dienes Removed % | Paraffin make wt % |
|---|---|---|---|---|
| W = 2/G = 35 | 52 | 34 | 77 | 0.4 |
| W = 2/G = 45 | 49 | 35 | 72 | 0.5 |
| W = 1/G = 10 | 56 | 38 | 80 | 0.4 |
| W = 1/G = 20 | 70 | 48 | 76 | 0.5 |

The results demonstrate effective hydrogenation of dienes with minimal paraffin make with the branched olefin feed. Increased diene hydrogenation was obtained at lower feed flows, and in this regime the paraffin make was controlled to the desired low level by minimizing the gas flow. Further results were obtained with a topped-branched feed as a function of feed flow as shown below.

| WHSV | Diene Removal % |
|---|---|
| 2 | 32 |
| 1 | 45 |
| 0.5 | 64 |
| 0.25 | 74 |

These results further demonstrate increased diene hydrogenation at low feed rates. From the foregoing, it was determined that a WHSV of 0.5 would balance paraffin make (0.5 wt %) and the need to remove only the most active dienes from the feed.

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

We claim:

1. A process for making a selectively branched alcohol composition, comprising:
   providing a lower olefin feed comprising linear olefins having at least 3 carbon atoms and a concentration of phosphorous-containing compounds;
   contacting said lower olefin feed with a sorbent comprising a metal selected from the group consisting of Sc, Ti, V, Cr, Fe, Co, Ni, Cu, Zn, Nb, Mn, Ag and combinations thereof on a support in an amount and under sorbing conditions effective to substantially reduce said concentration of said phosphorous-containing compounds in said lower olefin feed, producing a purified lower olefin feed;
   contacting said purified lower olefin feed with a skeletal isomerization catalyst under isomerization conditions effective to produce selectively branched olefins having up to about 36 carbon atoms, said selectively branched olefins comprising a quantity of dienes;
   reducing said quantity of dienes, thereby producing purified selectively branched olefins; and,
   converting said purified selectively branched olefins to said selectively branched alcohol composition.

2. The process of claim 1 wherein said reducing said quantity of dienes comprises contacting said selectively branched olefins with a hydrogenation catalyst that is sensitive to diene poisoning in the presence of a gas feed comprising an inert gas and a quantity of hydrogen at a flow rate and under hydrogenation conditions effective to convert a majority of dienes present in said selectively branched olefins to olefins while producing 1 wt. % or less paraffins, producing purified selectively branched olefins.

3. The process of claim 1 wherein said purified lower olefin feed comprises a second quantity of dienes, said process further comprising reducing said second concentration of dienes before contacting said purified lower olefin feed with said skeletal isomerization catalyst.

4. The process of claim 2 wherein said purified lower olefin feed comprises a second quantity of dienes, said process further comprises reducing said second concentration of dienes before contacting said purified lower olefin feed with said skeletal isomerization catalyst.

5. The process of claim 1 wherein said metal is selected from the group consisting of copper, silver, and a combination thereof.

6. The process of claim 2 wherein said metal is selected from the group consisting of copper, silver, and a combination thereof.

7. The process of claim 3 wherein said metal is selected from the group consisting of copper, silver, and a combination thereof.

8. The process of claim 4 wherein said metal is selected from the group consisting of copper, silver, and a combination thereof.

9. The process of claim 1 wherein
said converting comprises contacting said purified selectively branched olefins with a hydroformylation catalyst under hydroformylation conditions; and
a catalyst selected from the group consisting of said hydroformylation catalyst and said hydrogenation catalyst comprises palladium.

10. The process of claim 2 wherein
said converting comprises contacting said purified selectively branched olefins with a hydroformylation catalyst under hydroformylation conditions; and
a catalyst selected from the group consisting of said hydroformylation catalyst and said hydrogenation catalyst comprises palladium.

11. The process of claim 5 wherein
said converting comprises contacting said purified selectively branched olefins with a hydroformylation catalyst under hydroformylation conditions; and
a catalyst selected from the group consisting of said hydroformylation catalyst and said hydrogenation catalyst comprises palladium.

12. The process of claim 6 wherein
said converting comprises contacting said purified selectively branched olefins with a hydroformylation catalyst under hydroformylation conditions; and
a catalyst selected from the group consisting of said hydroformylation catalyst and said hydrogenation catalyst comprises palladium.

13. The process of claim 2 wherein said quantity is from about 2 to about 6 vol. % hydrogen.

14. The process of claim 13 wherein said flowrate is about 1 LHSV or less.

15. The process of claim 6 wherein said quantity is from about 2 to about 6 vol. % hydrogen.

16. The process of claim 15 wherein said flowrate is about 1 LHSV or less.

17. A process for making a selectively branched alcohol composition, comprising:
providing a lower olefin feed comprising linear olefins having at least 3 carbon atoms and a concentration of phosphorous-containing compounds;
contacting said lower olefin feed with a sorbent comprising copper oxide on a support in an amount and under sorbing conditions effective to substantially reduce said concentration of said phosphorous-containing compounds, producing a purified lower olefin feed;
contacting said purified lower olefin feed with a skeletal isomerization catalyst under isomerization conditions effective to produce selectively branched olefins having up to about 36 carbon atoms, said selectively branched olefins comprising a quantity of dienes;
reducing said quantity of dienes, thereby producing purified selectively branched olefins; and
converting said purified selectively branched olefins to said selectively branched alcohol composition.

18. The process of claim 17 wherein said reducing said quantity of dienes comprises contacting said selectively branched olefins with a hydrogenation catalyst that is sensitive to diene poisoning in the presence of a gas feed comprising an inert gas and a quantity of hydrogen under hydrogenation conditions and at a flowrate effective to convert to olefins a majority of dienes present in said selectively branched olefins while producing 1 wt. % or less paraffins, thereby producing purified selectively branched olefins.

19. The process of claim 17 wherein said purified lower olefin feed comprises a second quantity of dienes, said process further comprises reducing said second concentration of dienes before contacting said purified lower olefin feed with said skeletal isomerization catalyst.

20. The process of claim 18 wherein said purified lower olefin feed comprises a second quantity of dienes, said process further comprises reducing said second concentration of dienes before contacting said purified lower olefin feed with said skeletal isomerization catalyst.

21. The process of claim 17 wherein said sorbent comprises particles having a diameter of about 0.8 mm to about 1.6 mm and a length of from about 3 mm to about 5 mm.

22. The process of claim 17 wherein
said converting comprises contacting said purified selectively branched olefins with a hydroformylation catalyst under hydroformylation conditions; and
a catalyst selected from the group consisting of said hydroformylation catalyst and said hydrogenation catalyst comprises palladium.

23. The process of claim 18 wherein
said converting comprises contacting said purified selectively branched olefins with a hydroformylation catalyst under hydroformylation conditions; and
a catalyst selected from the group consisting of said hydroformylation catalyst and said hydrogenation catalyst comprises palladium.

24. The process of claim 17 wherein said lower olefin feed consists essentially of olefins having from about 14 to about 18 carbon atoms, 50 mol. % or more of said olefins being linear olefins.

25. The process of claim 17 wherein said selectively branched alcohol composition has an average number of branches per molecule of from about 0.5 to about 3 and less than 0.5 atom % of quaternary carbon atoms, said branching comprising methyl and ethyl branching.

26. The process of claim 17 wherein said sorbent is an acidic sorbent.

27. The process of claim 17 wherein said sorbing conditions comprise passing said lower olefin feed through a packed bed of said sorbent at a weight hourly space velocity of from about 0.1 per hour to about 5 per hour.

28. The process of claim 17 wherein said sorbent comprises from about 8 wt. % to about 20 wt. % of said copper oxide.

29. The process of claim 17 wherein said sorbent comprises from about 8 wt. % to about 10 wt. % of said copper oxide.

30. The process of claim 17 wherein said purified lower olefin feed contains 1 ppm or less of said phosphorous-containing compounds.

31. The process of claim 17 wherein said purified lower olefin feed contains 0.5 ppm or less of said phosphorous-containing compounds.

32. The process of claim 17 wherein said purified lower olefin feed contains 0.1 ppm or less of said phosphorous-containing compounds.

33. The process of claim 17 wherein said process produces a purified selectively branched olefin stream comprising about 40% of said quantity of dienes or less and a paraffin content of about 1 wt. % or less.

34. A process for making a selectively branched alcohol composition, comprising:
    providing a lower olefin feed comprising linear olefins having at least 3 carbon atoms and a concentration of phosphorous-containing compounds;
    contacting said lower olefin feed with a sorbent comprising copper oxide on a support in an amount and under conditions effective to substantially reduce said concentration of phosphorous-containing compounds in said lower olefin feed, producing a purified lower olefin feed;
    contacting said purified lower olefin feed with a skeletal isomerization catalyst under isomerization conditions effective to produce selectively branched olefins having up to about 36 carbon atoms;
    contacting said selectively branched olefins with a hydrogenation catalyst that is sensitive to diene poisoning in the presence of a gas feed comprising an inert gas, said gas feed also comprising from about 2 to about 6 vol. % hydrogen, at a feedstock flow rate of about 1 LHSV or less; and
    contacting said selectively branched olefins with a hydroformylation catalyst comprising palladium under hydroformylation conditions, thereby producing said selectively branched alcohol composition.

35. The process of claim 34 wherein said support comprises alumina.

36. The process of claim 35 wherein said sorbent comprises particles having a diameter of about 0.8 mm and a length of from about 3 mm to about 5 mm.

37. The process of claim 34 wherein said lower olefin feed consists essentially of olefins having at least 11 carbon atoms, 50 mol. % or more of said olefins being linear olefins.

38. The process of claim 34 wherein said lower olefin feed consists essentially of olefins having from about 14 to about 18 carbon atoms, 50 mol. % or more of said olefins being linear olefins.

39. The process of claim 34 wherein said selectively branched alcohol composition has an average number of branches per molecule of from about 0.5 to about 3 and less than 0.5 atom % of quaternary carbon atoms, said branching comprising methyl and ethyl branching.

40. The process of claim 34 wherein said sorbent is an acidic sorbent.

41. The process of claim 35 wherein said sorbent is an acidic sorbent.

42. The process of claim 34 wherein said sorbing conditions comprise passing said lower olefin feed through a packed bed of said sorbent at a weight hourly space velocity of from about 0.1 per hour to about 5 per hour.

43. The process of claim 34 wherein said sorbent comprises from about 8 wt. % to about 20 wt. % of said copper oxide.

44. The process of claim 34 wherein said sorbent comprises from about 8 wt. % to about 10 wt. % of said copper oxide.

45. The process of claim 34 wherein said hydrogenation conditions comprise
    a reaction pressure of from about 20 to about 200 psig; and,
    a reaction temperature of from about 0° C. (32° F.) to about 100° C. (212° F.).

46. The process of claim 34 wherein said purified olefin feed contains 1 ppm or less of said phosphorous-containing compounds.

47. The process of claim 34 wherein said purified olefin feed contains 0.5 ppm or less of said phosphorous-containing compounds.

48. The process of claim 34 wherein said hydrogenation catalyst comprises about 0.2 wt. % palladium on a suitable support.

49. The process of claim 48 wherein said feedstock flow rate is about 0.5 LHSV or less.

50. The process of claim 34 wherein said process produces a purified selectively branched olefin stream comprising about 40% of said quantity of dienes or less and a paraffin content of about 1 wt. % or less.

51. The process of claim 34 wherein said hydrogenation catalyst comprises particles having a diameter of about 0.8 mm and a length of from about 3 mm to about 5 mm.

* * * * *